US00PP09190P

United States Patent [19]

Dehan

[11] Patent Number: Plant 9,190

[45] Date of Patent: Jul. 4, 1995

[54] IMPATIENS PLANT NAMED 'SYRTAKI'

[75] Inventor: Klara Dehan, Holon, Israel

[73] Assignee: Danziger—"Dan" Flower Farm, Moshav Mishmar Hashiva, Israel

[21] Appl. No.: 315,820

[22] Filed: Sep. 20, 1994

[51] Int. Cl.[6] ..... A01H 5/00

[52] U.S. Cl. ..... Plt./87.6

[58] Field of Search ..... Plt. 87.6

*Primary Examiner*—James R. Feyrer

[57] ABSTRACT

A distinct cultivar of Impatiens plant named Syrtaki, characterized by its medium to large rounded red purlpe flowers; uniformly compact and mounded plant habit; freely branching growth habit; medium green, non-variegated foliage; medium leaf size; and early flowering.

1 Drawing Sheet

The present invention relates to a new and distinctive cultivar of New Guinea Impatiens, botanically known as *Impatiens hawkeri,* and hereinafter referred to by the cultivar name Syrtaki.

The new cultivar was developed by me in a controlled breeding program at Danziger—"Dan" Flower Farm, Mishmar Hashiva, Israel, by crossing the female, or seed, parent identified as *Impatiens hawkeri* DAN 6079-3 with the male, or pollen, parent identified as *Impatiens hawkeri* DAN 9670-3. Both parents are non-patented selections developed by me in a controlled breeding program and used only as breeding parents.

Asexual reproduction of the new cultivar by terminal cuttings taken by me at Mishmar Hashiva, Israel, has shown that the combination of features of this new Impatiens are firmly fixed and retained through successive generations of asexual reproduction.

The following characteristics are repeatedly observed and are determined to be the distinctive and unique characteristics of Syrtaki. These characteristics in combination distinguish Syrtaki from both its parent varieties and other cultivated New Guinea Impatiens used in the floriculture industry:

1. Medium to large size, rounded red purple flowers.
2. Uniformly compact and mounded plant habit.
3. Freely branching habit.
4. Medium green, non-variegated foliage.
5. Medium leaf size.
6. Early flowering.

The new cultivar is most similar to the patented *Impatiens hawkeri* cultivar Samba (U.S. Plant Pat. No. 8,110) in flower color. However Syrtaki differs from Samba in its more compact growth habit, more lateral branches, smaller leaves, and smaller but more rounded flowers.

The accompanying colored photograph illustrates the overall appearance and flower color of the new cultivar, showing the colors as true as it is reasonably possible to obtain in colored reproductions of this type. The flower color in the photograph is more red than the actual flower color. The photograph constitutes a top perspective view of a typical potted plant of Syrtaki.

In the following decription, color references are made to The Royal Horticultural Society Colour Chart except where general terms of ordinary dictionary significancce are used. The following observations, measurements and comparisons describe plants grown in Mishmar Hashiva, Israel, under commercial practice in a polyethylene-covered greenhouse with minimum temperatures of 12° to 14° C. during the winter and maximum temperatures of 35° C. during the summer. Average light levels in the greenhouse is 40,000 lux. Syrtaki has not been observed under all possible environmental conditions. The phenotype may vary significantly with variations in environment such as temperature, light intensity and daylength.

Botanical classification: *Impatiens hawkeri* cultivar Syrtaki.

Parentage:

*Female (seed) parent.13 Impatiens hawkeri* DAN 6079-3.

*Male (pollen) parent.—Impatiens hawkeri* DAN 9670-3.

Propagation:

A. *Type.*—Terminal tip cuttings.

B. *Time to initiate roots.*—1. Summer: 7 days at 25° C. 2. Winter: 9 days at 20° C.

C. *Rooting habit.*—Fibrous and well-branched.

Plant description:

A. *General appearance.*—Compact and mounded plant habit; freely branching; suitable for 10 cm pots and small hanging baskets.

B. *Foliage description.*—1. Shape: Lanceolate with acuminate tip and attenuate base. 2. Size: a. Length: 8 cm. b. Width: 2.5 cm. 3. Texture: Smooth and shiny. 4. Margin: Finely serrated. 5. Color: a. Young foliage, upper surface: 137A. b. Young foliage, under surface: 138B. c. Mature foliage, upper surface: 137A. d. Mature foliage, under surface: 138B. e. Veins, upper surface: 46A. f. Veins, under surface: 46A.

C. *Stem description.*—1. Internode length: 3.5 cm. 2. Stem color: 59D.

Flowering description:

A. *Flowering habit.*—Freely flowering.

B. *Natural flowering season.*—Year-round. Early flowering: under summer conditions, plants flower 8 to 9 weeks after planting; and under winter conditions, plants flower 12 to 13 weeks after planting.

C. *Flowers borne.*—Flower buds develop in leaf axils. Open flowers are displayed above the foliage.

D. *Quantity of inflorescences.*—Very floriferous; usually 3 to 4 flowers per axil and about 10 to 12 flowers per lateral branch at various stages of development; usually at least 2 fully open flowers per lateral branch.

E. *Flower opening rate.*—From bud initiation, flowers are fully open after 5 to 10 days depending on temperature, humidity and light level.

F. *Flower size.*—1. Length: 5.5 cm. 2. Width: 5.5 cm.

G. *Petals.*—1. Shape: Cordate. 2. Quantity: 5. 3. Color: a. When opening: 66A. b. Upper surface: 66A. c. Under surface: 67B. d. Fading to: 66A.

H. *Flower bud.*—1. Shape: Round with spur. 2. Color: 60B.

I. *Spur.*—1. Shape: Needle-shaped, curved at end. 2. Color: 60B. 3. Length: a. On flower bud: 1.3 cm. b. On opened flower: 3.6 cm.

J. *Reproductive organs.*—1. Androecium: a. Stamen number: 5. b. Anther shape: Oblong. c. Anther color: 60A. d. Pollen color: 155D. 2. Gynoecium: a. Stigma color: 143A. b. Style color: 143A. c. Ovary: Superior, 5-celled. d. Ovary color: 143A. e. Ovary size: 1 to 2 mm.

Disease resistance: No fungal or bacterial problems observed.

Seed development: Seed production is very rarely observed.

I claim:

1. A new and distinct cultivar of Impatiens plant named Syrtaki, as illustrated and described.

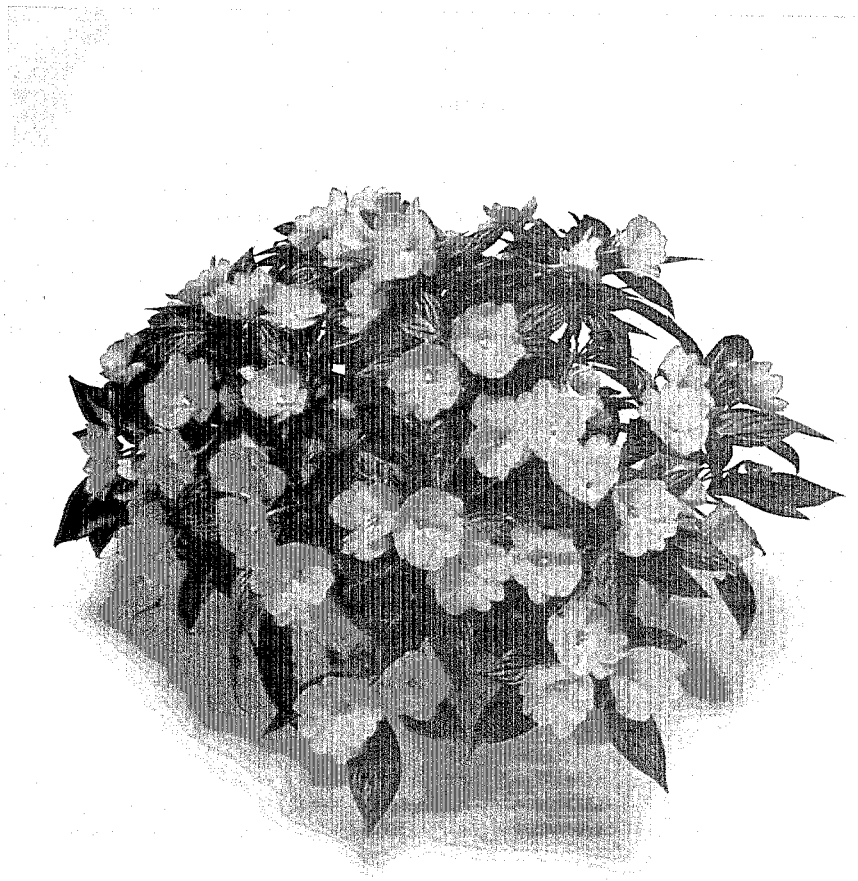

* * * * *